US010595736B1

(12) United States Patent
Villongco

(10) Patent No.: US 10,595,736 B1
(45) Date of Patent: Mar. 24, 2020

(54) HEART GRAPHIC DISPLAY SYSTEM

(71) Applicant: Vektor Medical, Inc., Carlsbad, CA (US)

(72) Inventor: Christopher Villongco, Oakland, CA (US)

(73) Assignee: VEKTOR MEDICAL, INC., Carlsbad, CA (US)

(*) Notice: Subject to any disclaimer, the term of this patent is extended or adjusted under 35 U.S.C. 154(b) by 0 days.

(21) Appl. No.: 16/436,460

(22) Filed: Jun. 10, 2019

(51) Int. Cl.
| | |
|---|---|
| *A61B 5/00* | (2006.01) |
| *A61B 5/04* | (2006.01) |
| *A61B 5/0456* | (2006.01) |
| *A61B 5/044* | (2006.01) |
| *A61B 5/0452* | (2006.01) |
| *A61B 5/0468* | (2006.01) |
| *A61B 5/046* | (2006.01) |
| *G16H 50/20* | (2018.01) |
| *G06N 20/00* | (2019.01) |
| *A61B 5/0472* | (2006.01) |

(52) U.S. Cl.
CPC .......... *A61B 5/04007* (2013.01); *A61B 5/044* (2013.01); *A61B 5/0456* (2013.01); *A61B 5/04525* (2013.01); *A61B 5/7267* (2013.01); *A61B 5/743* (2013.01); *A61B 5/046* (2013.01); *A61B 5/0468* (2013.01); *A61B 5/0472* (2013.01); *G06N 20/00* (2019.01); *G16H 50/20* (2018.01)

(58) Field of Classification Search
CPC ..... A61B 5/04007; A61B 5/743; A61B 5/044; A61B 5/0425; A61B 5/0456; A61B 5/7267; A61B 5/0472; A61B 5/0468; A61B 5/046; G06N 20/00; G16H 50/20
See application file for complete search history.

(56) References Cited

U.S. PATENT DOCUMENTS

| | | | |
|---|---|---|---|
| 5,458,116 A | 10/1995 | Egler | |
| 5,596,634 A | 1/1997 | Fernandez et al. | |

(Continued)

FOREIGN PATENT DOCUMENTS

WO 2015153832 A1 10/2015

OTHER PUBLICATIONS

Cobb, Leonard A., et al. "Changing incidence of out-of-hospital ventricular fibrillation, 1980-2000." Jama 288.23 (2002): 3008-3013.

(Continued)

*Primary Examiner* — Scott M. Getzow
(74) *Attorney, Agent, or Firm* — Perkins Coie LLP

(57) ABSTRACT

A system is provided for displaying heart graphic information relating to sources and source locations of a heart disorder to assist in evaluation of the heart disorder. A heart graphic display system provides an intra-cardiogram similarity ("ICS") graphic and a source location ("SL") graphic. The ICS graphic includes a grid with the x-axis and y-axis representing patient cycles of a patient cardiogram with the intersections of the patient cycle identifiers indicating similarity between the patient cycles. The SL graphic provides a representation of a heart with source locations indicated. The source locations are identified based on similarity of a patient cycle to library cycles of a library cardiogram of a library of cardiograms.

26 Claims, 12 Drawing Sheets
(2 of 12 Drawing Sheet(s) Filed in Color)

(56) References Cited

U.S. PATENT DOCUMENTS

| | | | |
|---|---|---|---|
| 6,269,336 | B1 | 7/2001 | Ladd et al. |
| 6,292,783 | B1 | 9/2001 | Rohler et al. |
| 6,324,513 | B1 | 11/2001 | Nagai et al. |
| 6,567,805 | B1 | 5/2003 | Johnson et al. |
| 6,895,084 | B1 | 5/2005 | Saylor et al. |
| 8,521,266 | B2 | 8/2013 | Narayan |
| 9,706,935 | B2 | 7/2017 | Spector |
| 2001/0049688 | A1 | 12/2001 | Fratkina et al. |
| 2002/0010679 | A1 | 1/2002 | Felsher |
| 2002/0154153 | A1 | 10/2002 | Messinger |
| 2002/0188599 | A1 | 12/2002 | McGreevy |
| 2003/0182124 | A1 | 9/2003 | Khan |
| 2004/0083092 | A1 | 4/2004 | Valles |
| 2004/0176697 | A1 | 9/2004 | Kappenberger |
| 2007/0032733 | A1 | 2/2007 | Burton |
| 2008/0140143 | A1* | 6/2008 | Ettori .............. A61B 5/04525 607/14 |
| 2009/0275850 | A1* | 11/2009 | Mehendale ........ A61B 5/04525 600/523 |
| 2011/0251505 | A1 | 10/2011 | Narayan |
| 2011/0307231 | A1 | 12/2011 | Kirchner |
| 2012/0173576 | A1 | 7/2012 | Gilliam et al. |
| 2013/0006131 | A1 | 1/2013 | Narayan |
| 2013/0096394 | A1 | 4/2013 | Gupta |
| 2013/0131529 | A1 | 5/2013 | Jia |
| 2013/0268284 | A1 | 10/2013 | Heck |
| 2014/0005562 | A1 | 1/2014 | Bunch |
| 2014/0200575 | A1 | 7/2014 | Spector |
| 2014/0276152 | A1 | 9/2014 | Narayan |
| 2015/0216432 | A1 | 8/2015 | Yang |
| 2015/0216434 | A1 | 8/2015 | Ghosh |
| 2015/0216438 | A1 | 8/2015 | Bokan et al. |
| 2016/0135706 | A1* | 5/2016 | Sullivan ............... A61B 5/0059 600/301 |
| 2016/0331337 | A1 | 11/2016 | Ben-Haim |
| 2017/0027649 | A1 | 2/2017 | Kiraly |
| 2017/0079542 | A1 | 3/2017 | Spector |
| 2017/0161439 | A1 | 6/2017 | Raduchel et al. |
| 2017/0178403 | A1 | 6/2017 | Krummen |
| 2017/0202421 | A1 | 7/2017 | Hwang et al. |
| 2017/0209698 | A1 | 7/2017 | Villongco |
| 2017/0319278 | A1 | 11/2017 | Trayanova |
| 2017/0367603 | A1 | 12/2017 | Spector |
| 2018/0020916 | A1 | 1/2018 | Ruppersberg |
| 2019/0104951 | A1 | 4/2019 | Valys |

OTHER PUBLICATIONS

Gonzales, Matthew J., et al. "Structural contributions to fibrillatory rotors in a patient-derived computational model of the atria." EP Europace 16.suppl 4 (2014): iv3-iv10.

Krishnamurthy, Adarsh, et al. "CRT Response is Greater in Patients With Larger Fraction of the Myocardium Performing Negative Regional Work." Circulation 128.Suppl 22 (2013): A11135-A11135, Abstract only.

Krishnamurthy, Adarsh, et al. "Patient-specific models of cardiac biomechanics." Journal of computational physics 244 (2013): 4-21.

Krummen, David E., et al. "Rotor stability separates sustained ventricular fibrillation from selfterminating episodes in humans." Journal of the American College of Cardiology 63.24 (2014): 2712-2721.

Nash, Martyn P., et al. "Evidence for multiple mechanisms in human ventricular fibrillation." Circulation 114.6 (2006): 536-542.

Ten Tusscher, K. H. W. J., et al. "A model for human ventricular tissue." American Journal of PhysioloQy-Heart and Circulatory PhysioloQy 286.4 (2004): H1573-H1589.

Villongco, Christopher T., et al. "Patient-specific modeling of ventricular activation pattern using surface ECG-derived vectorcardiogram in bundle branch block." Progress in biophysics and molecular bioloQy 115.2 (2014): 305-313.

Vadakkumpadan, Fijoy, et al. "Image-based estimation of ventricular fiber orientations for personalized modeling of cardiac electrophysiology." IEEE-TMI 31.5 (2012): 1051-1060.

Taggart, Peter, et al. "Developing a novel comprehensive framework for the investigation of cellular and whole heart electrophysiology in the in situ human heart: Historical perspectives, current progress and future prospects. " Progress in biophysics and molecular biology 115.2-3 (2014): 252-260.

Tobon, Catalina, et al. "Dominant frequency and organization index maps in a realistic three-dimensional computational model of atrial fibrillation." Europace 14.suppl_5 (2012): v25-v32.

Kors, J.A., et al., "Recontruction of the Frank vectorcardiogram from standard electrocardiographic leads: diagnostic comparison of different methods," European Heart Journal, vol. 11, Issue 12, Dec. 1, 1990, pp. 1083-1092.

Tomašić, Ivan et al., "Electrocardiographic Systems With Reduced Numbers of Leads—Synthesis of the 12-Lead ECG," IEEE Reviews in Biomedical Engineering, vol. 7, 2014, pp. 126-142.

Frank, Ernest, "An Accurate, Clinically Practical System for Spatial Vectorcardiography," American Heart Association, Inc., downloaded from http://circ.ahajournals.org/ at CONS California DIG LIB on Mar. 12, 2014.

Vozda, M. et al.., "Methods for derivation of orthogonal leads from 12-lead electrocardiogram: A review," Elsevier, Biomedical Signal Processing and Control 19 (2015), 23-34.

Si, Hang, "TetGen, a Delaunay-Based Quality Tetrahedral Mesh Generator," ACM Transactions on Mathematical Software, vol. 41, No. 2, Article 11, Jan. 2015, 36 pages.

Tajbakhsh, Nima et al., "Convolutional Neural Networks for Medical Image Analysis: Full Training or Fine Tuning?" IEEE Transactions on Medical Imaging (2016) vol. 35, e-pp. 1-17).

International Search Report and Written Opinion issued for PCT/US2019/029181 dated Sep. 16, 2019.

International Search Report and Written Opinion issued for PCT/US2019/029184 dated Sep. 24, 2019.

Carrault, Guy, et al. "A model-based approach for learning to identify cardia arrhythias," Joint European Conference on Artificial Intellegence in Medicine and Medicine Decision Making. Springer, Berline Heidelberg, 1999.

Carrualt, Guy, et al. "Temporal abstraction and inductive logic programming for arrhythima recognition from electrocardiograms." Artificial intelligence in medicine 28.3 (2003): 231-263.

Hren, Rok, et al. "Value of simulated body surface potential maps as templates in localizing sites of ectopic activation for radiofrequency ablation" Physiol. Meas. 18 (1997) 373-400. Mar. 7, 1997.

International Search Report and Written Opinion issued for PCT/US16/68449 dated Mar. 29, 2017.

Siregar, P. "An Interactive Qualitative Model in Cardiology" Computers and Biomedical Research 28, pp. 443-478, May 16, 1994.

* cited by examiner

HEART GRAPHIC DISPLAY SYSTEM

CROSS-REFERENCE TO RELATED APPLICATIONS

This application is related to the following applications: U.S. Provisional Application No. 62/663,049, filed on Apr. 26, 2018, entitled "MACHINE LEARNING USING SIMULATED CARDIOGRAMS;" U.S. Provisional Application No. 62/760,561, filed Nov. 13, 2018, entitled "RECORD ABLATION PROCEDURE RESULTS IN A DISTRIBUTED LEDGER;" U.S. application Ser. No. 16/042,984, filed Jul. 23, 2018, entitled "GENERATING SIMULATED ANATOMIES OF AN ELECTROMAGNETIC SOURCE;" U.S. application Ser. No. 16/042,953, filed Jul. 23, 2018, entitled "GENERATING A MODEL LIBRARY OF MODELS OF AN ELECTROMAGNETIC SOURCE;" U.S. application Ser. No. 16/042,973, filed Jul. 23, 2018, and entitled "USER INTERFACE FOR PRESENTING SIMULATED ANATOMIES OF AN ELECTROMAGNETIC SOURCE;" U.S. application Ser. No. 16/042,993, filed Jul. 23, 2018, entitled "CONVERTING A POLYHEDRAL MESH REPRESENTING AN ELECTROMAGNETIC SOURCE;" U.S. application Ser. No. 16/043,011, filed Jul. 23, 2018, entitled "GENERATING APPROXIMATIONS OF CARDIOGRAMS FROM DIFFERENT SOURCE CONFIGURATIONS;" U.S. application Ser. No. 16/043,022, filed Jul. 23, 2018, entitled "BOOTSTRAPPING A SIMULATION-BASED ELECTROMAGNETIC OUTPUT OF A DIFFERENT ANATOMY;" U.S. application Ser. No. 16/043,034, filed Jul. 23, 2018, entitled "IDENTIFYING AN ATTRIBUTE OF AN ELECTROMAGNETIC SOURCE CONFIGURATION BY MATCHING SIMULATED AND PATIENT DATA;" U.S. application Ser. No. 16/043,041, filed Jul. 23, 2018, entitled "MACHINE LEARNING USING CLINICAL AND SIMULATED DATA;" U.S. application Ser. No. 16/043,050, filed Jul. 23, 2018, entitled "DISPLAY OF AN ELECTROMAGNETIC SOURCE BASED ON A PATIENT-SPECIFIC MODEL;" U.S. application Ser. No. 16/043,054, filed Jul. 23, 2018, entitled "DISPLAY OF AN ELECTRICAL FORCE GENERATED BY AN ELECTRICAL SOURCE WITHIN A BODY;" U.S. application Ser. No. 16/162,695, filed Oct. 17, 2018, entitled "MACHINE LEARNING USING SIMULATED CARDIOGRAMS;" U.S. application Ser. No. 16/206,005, filed Nov. 30, 2018, entitled "CALIBRATION OF SIMULATED CARDIOGRAMS;", U.S. application Ser. No. 16/247,463, filed Jan. 14, 2019, entitled "IDENTIFY ABLATION PATTERN FOR USE IN AN ABLATION; each are hereby incorporated by reference in their entirety.

BACKGROUND

Many heart disorders can cause symptoms, morbidity (e.g., syncope or stroke), and mortality. Common heart disorders caused by arrhythmias include inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT"). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant episodes. Arrhythmias can be treated with ablation using different technologies, including radiofrequency energy ablation, cryoablation, ultrasound ablation, laser ablation, external radiation sources, directed gene therapy, and so on by targeting the source of the heart disorder. Since the sources of heart disorders and the locations of the source vary from patient to patient, even for common heart disorders, targeted therapies require the source of the arrhythmia to be identified.

Unfortunately, current methods for reliably identifying the sources and their source locations of a heart disorder can be complex, cumbersome, and expensive. For example, one method uses an electrophysiology catheter having a multielectrode basket catheter that is inserted into the heart (e.g., left ventricle) intravascularly to collect from within the heart measurements of the electrical activity of the heart, such as during an induced episode of VF. The measurements can then be analyzed to help identify a possible source location. Presently, electrophysiology catheters are expensive (and generally limited to a single use) and may lead to serious complications, including cardiac perforation and tamponade. Another method uses an exterior body surface vest with electrodes to collect measurements from the patient's body surface, which can be analyzed to help identify an arrhythmia source location. Such body surface vests are expensive, are complex and difficult to manufacture, and may interfere with the placement of defibrillator pads needed after inducing VF to collect measurements during the arrhythmia. In addition, the vest analysis requires a computed tomography ("CT") scan and is unable to sense the interventricular and interatrial septa where approximately 20% of arrhythmia sources may occur.

BRIEF DESCRIPTION OF THE DRAWINGS

This application contains at least one drawing executed in color. Copies of this application with color drawing(s) will be provided by the Office upon request and payment of the necessary fees.

DETAILED DESCRIPTION

Methods and systems are provided for displaying electromagnetic ("EM") source graphic information relating to sources and source locations of patterns (abnormal or normal) of electrical activity of an EM source within a body. A body may be, for example, a human body, and the EM source may be a heart, a brain, a liver, a lung, a kidney, a stomach, or another part of the body that generates an EM field that can be measured, preferably, from outside the body and represented by EM measurements such as a cardiogram represented by an electrocardiogram ("ECG") or a vectorcardiogram ("VCG") and an electroencephalogram ("EEG"). In the following, an EM graphic display system is described primarily in the context of an EM source that is a heart. The methods and systems of the EM graphic system described below for the heart can be employed and adapted to provide graphics of other EM sources of a body. For example, the identification of cycles of a cardiogram as described below can be adapted to identify cycles of an EEG or cycles of EM measurements representing the EM field of a stomach. A graphic provides visual indications that can be textual and non-textual (e.g., pictorial, animation, and computer-generated rendering).

Figure 1:
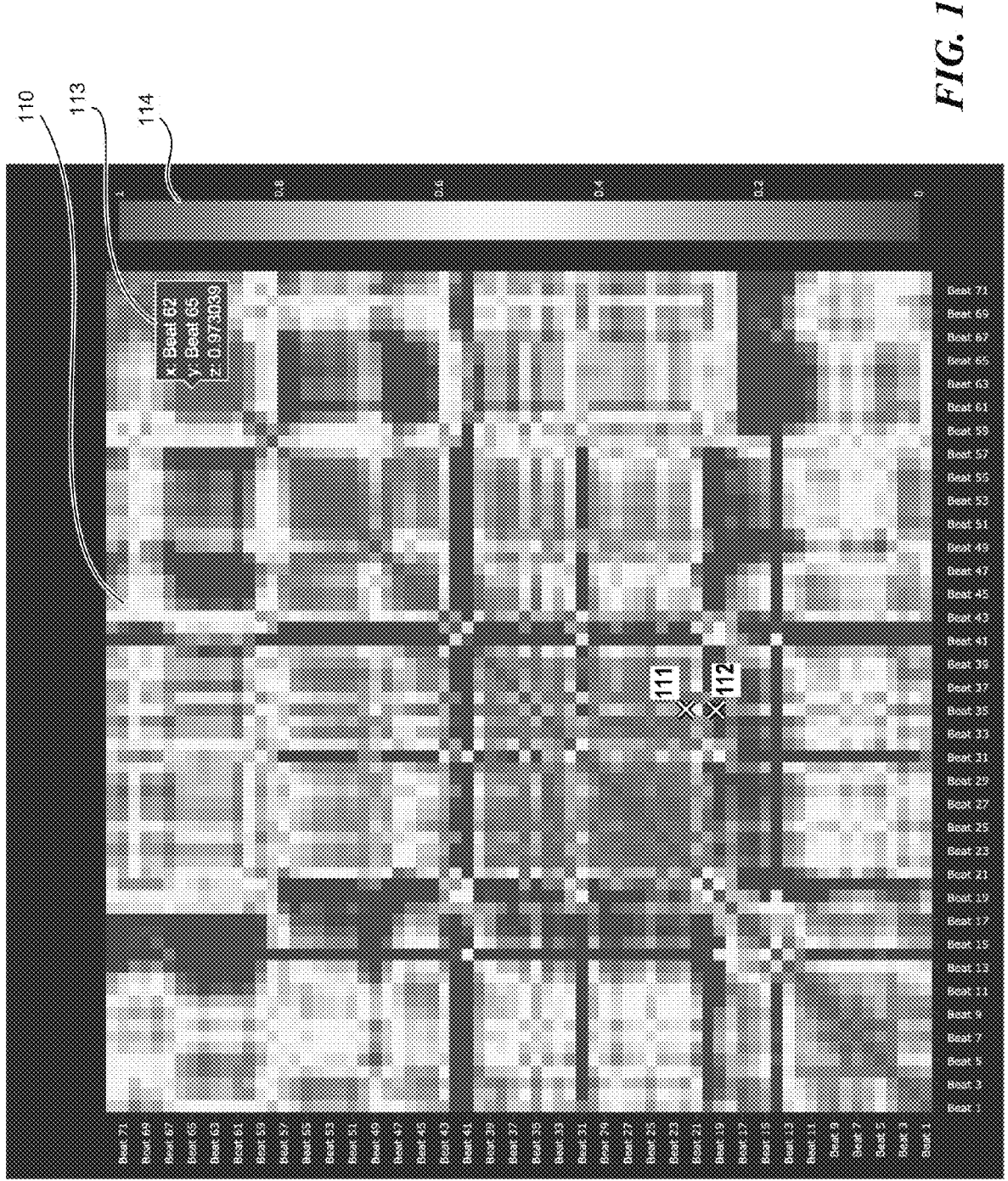
FIG. 1 illustrates an ICS graphic in some embodiments.

In some embodiments, methods and systems are provided for displaying heart graphic information relating to sources and source locations of heart disorders to assist in evaluation of heart disorders. In some embodiments, a heart graphic display ("HGD") system provides an intra-cardiogram similarity ("ICS") graphic and a source location ("SL") graphic. The ICS graphic provides information on the similarity between cycles of a cardiogram (e.g., of a patient). FIG. 1 illustrates an example ICS graphic in some embodiments. The ICS graphic 100 includes a similarity map 110 that provides visual information on the similarity between pairs of patient cycles of a patient cardiogram of a patient. The x-axis and the y-axis represent the patient cycles (e.g., beats), and the intersections of a first patient cycle and a second patient cycle represent the similarity between the first patient cycle and the second patient cycle. The color in the area at the intersection of a patient cycle of the x-axis and a patient cycle of the y-axis represents a similarity score (e.g., based on a Pearson correlation coefficient or a cosine similarity) indicating the similarity between those patient cycles. The similarity scores may range from 0 to 1 with 1 being the similarity score of identical patient cycles. Legend 114 of the ICS graphic illustrates the color range representing the similarity scores with red representing the lowest similarity score and blue representing the highest similarity score. (The similarity scores may be represented by similarity indicators based on graphic characteristics other than color such as using a grayscale, a range polyhedron from a triangle to a circle, and so on.) As an example, the intersection 111 of cycle 35 and cycle 22 is blue indicating a relatively high similarity between those patient cycles. The intersection 112 of cycle 35 and cycle 20 is red indicating a relatively low similarity between those patient cycles. The intersections along the diagonal represent the similarly of each patient cycle to itself and is thus dark blue indicating a similarity score of 1. The similarity map may be considered to correspond to a symmetric matrix. Popup 113 identifies, when a pointer is moved over an intersection, the cycles of the x-axis and the y-axis of the intersection and the similarity score of those cycles as a z-axis value. When a pointer selects a window or range of beats, a popup can also display statistical summaries of the similarity scores within the window such as similarity score average and standard deviation, number of significantly different groups of similar cycles, a stability index, or arrhythmia type classification. The ICS graphic may also be generated based on library cycles of a library cardiogram of a library of cardiograms (described below).

The stability index (or stability feature) for a source is a measure of the cycle-to-cycle consistency of a dominant arrhythmia source localized to a particular region in the heart. The stability index may be based on the similarity scores of a sequence of consecutive cycles and represented by the standard deviation of all similarity scores either above or below the identity diagonal of the ICS graphic within a user-defined time interval. A high mean and a low standard deviation indicate a stable arrhythmia (e.g., focal tachycardia), and a low mean and high standard deviation indicates an unstable arrhythmia (e.g., rotor fibrillation). The measure may be a count of the number of off-diagonal clusters with high similarity to estimate the number of unique arrhythmia activation patterns and therefore sources. A technique for determining the stability of arrhythmia sources is described in Krummen, D., et. al., Rotor Stability Separates Sustained Ventricular Fibrillation From Self-Terminating Episodes in Humans, Journal of American College of Cardiology, Vol. 63, No. 23, 2014, which is hereby incorporated by reference.

The ICS graphic is useful to identify characteristic electrical activation dynamics to help eliminate the driving mechanisms of a clinical arrhythmia. An effective target source stability index or arrhythmia type classification may be indicated by the persistence of similar patient cycles. Such similar patient cycles may indicate consistent, periodic electrical activation dynamics within the heart. Electrical activation dynamics (i.e., how action potentials propagate through the cardiac tissue) are influenced by a number of factors including electrical properties of the cardiac tissue, source location, source type (e.g., rotor or focal, fibrillation, tachycardia, flutter, etc.), and disease substrate (e.g., scar). Given these factors, the similarity between patient cycles may not necessarily indicate a rotor-based arrhythmia source, but it may more generally indicate which electrical activation patterns in the cardiogram are more or less dominant or prevalent. Dominant electrical activation patterns that appear frequently in the cardiogram indicate driving, sustaining mechanisms of an arrhythmia.

Analysis of an ICS graphic may show multiple driving mechanisms as multiple groupings of similar patient cycles. When multiple groupings occur in a time-continuous sequence (consecutive groupings of high similarity scores close to the diagonal of identity of the similarity map), the analysis may suggest a transition of electrical activation dynamics from one grouping to the next. This transition may be due to movement of the source location or a change from one arrhythmia type to another (e.g. rotor-based VF can evolve into a focal-source VT). For example, referring to FIG. 1, the intersections of x-axis cycles 22-29 and y-axis cycles 22-29 represent a grouping of similar patient cycles and the intersections of x-axis cycles 33-40 and y-axis cycles 33-40 represent another grouping of similar cycles. The intersections of x-axis cycles 22-29 and y-axis cycles 33-40 indicate similarity of these groupings also referred to as off-diagonal clusters. It is possible to have multiple distant arrhythmia sources or types in the heart that do not represent movement of a single driving mechanism. An indication of multiple driving mechanisms may be present if multiple groupings of similar patient cycles do not occur in a time-continuous sequence and the estimated source locations from the localization analysis are distant. For example, the grouping represented by x-axis cycles 22-29 and y-axis cycles 22-29 and the grouping represented by x-axis cycles 49-56 and y-axis cycles 49-56 are not in a time-continuous sequence. In other cases, groupings not in a time-continuous sequence may turn out to be the same arrhythmia pattern and therefore suggest a common driving mechanism. Such a common driving mechanism may be indicated by a grouping of high similarity on the off-diagonal portions of the similarity map. For example, the grouping represented by x-axis cycles 22-29 and y-axis cycles 49-56 indicates the similarity of the grouping represented by x-axis cycles 22-29 and y-axis cycles 22-29 and the grouping representing by x-axis cycles 49-56 and y-axis cycles 49-56, which are not in a time-continuous sequence. If the similarity is low between groupings of similar cycles not in time-continuous sequence, the analysis may suggest multiple independent driving mechanisms.

Figure 2:
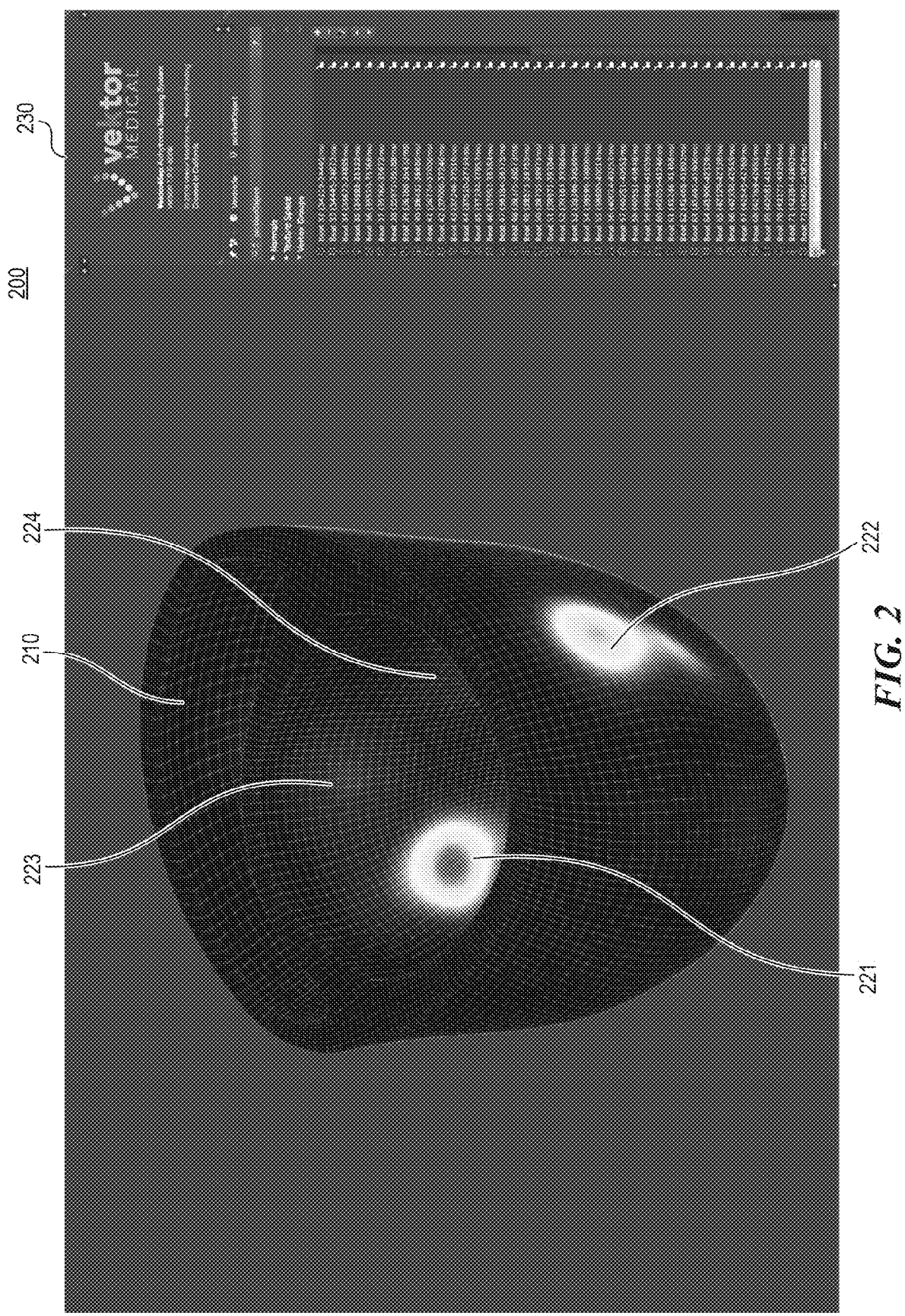
FIG. 2 illustrates an SL graphic in some embodiments.

The SL graphic provides information relating to source locations identified by comparing patient cycles of a patient cardiogram to library cycles of a library of cardiograms. Each library cycle is associated with a source location and type. FIG. 2 illustrates an example SL graphic in some embodiments. SL graphic 200 includes a representation of a heart (e.g., a ventricle) 210 along with source location indicators 221-224 derived from one or more patient cycles. To identify the source locations or types to include in the SL graphic, the HGD system calculates similarity scores indicating similarity between library cycles and patient cycles of a patient cardiogram of the patient. The HGD system then identifies some number (i.e., one or more) of source locations associated with library cycles (referred as target library cycles) based on their similarity scores. For example, the HGD system may identify source locations based on the highest similarity score of the library cycles associated with each source location, based on the average of the four highest similarity scores of the library cycles associated with each source location, and so on. Source locations associated with the library cycles having the highest similarity scores are likely to be more informative in assisting the evaluation of a heart disorder. The HGD system then generates the SL graphic that includes a representation of a portion of a heart and a source location and type indicator for each source location and type of a target library cycle.

In some embodiments, the source location and type indicators may have characteristics that vary based on similarity scores associated with the source location and type indicators. The source location and type indicators may be centered on the source locations. The source location indicators may be circles with characteristics such as size of the circle and color of the circle. The size of the circle may be based on a similarity score associated with the target library cycles. A circle with a small size (i.e., radius) that is centered on a source location may indicate that a target library cycle associated with that source location and type has a high similarity score. (A source location and type associated with a target library cycle is considered to be associated with the similarity score of that target library cycle.) A small size may indicate greater confidence in the relevance of the source location. The HGD system may assign a color to each source location and type indicator to indicate the relative ordering of the similarity scores of the source locations. For example, assuming four source location indicators are displayed, the source location indicator associated with the highest similarity score may be assigned the color red, and the other three source location indicators may be assigned the colors yellow, green, and blue in decreasing order of their associated similarity scores. The HGD system may set the center of the circle to the color assigned to a source location indicator and vary the color assigned to remainder of the circle linearly from the color assigned to the center to the color indicating the smallest similarity score at the circumference of the circle. For example, the coloring of the circles may vary from red to blue, yellow to blue, green to blue, and solid blue. The source location indicators may be in shapes other than circles and may be based on a grayscale rather than a range of colors. A source location indicator may be selected from a list of source location indicators 230. Each item in the list of source location indicators may be labeled by the cycle/beat number, cycle start and end times, a similarity statistic, or a description of the source type.

In some embodiments, the HGD system may include in the SL graphic source locations derived from multiple patient cycles. For example, the HGD system may identify source locations for multiple patient cycles and include source location indicators for the multiple patient cycles on the SL graphic simultaneously. Alternatively, the HGD system may generate a source location indicator for each patient cycle and output the source location indicators in sequence to present an animation of the source locations as they move from patient cycle to patient cycle. When the SL graphic includes source locations for multiple patient cycle simultaneously, some of the source location indicators may overlap. In such a case, the HGD system may set a pixel of an overlapping portion to an average of the colors for that pixel from the overlapping source location indicators. For example, if the colors for a pixel is yellow in one source location indicator and blue in the other source location indicator, the color for the pixel of the LS graphic may be green. A cycle selection box 230 of FIG. 2 allows a user to select one or more patient cycles to be used to identify the source locations for the SL graphic.

In some embodiments, the HGD system may identify source locations for multiple patient cycles by, for each source location, generating an average of the similarity scores associated with each patient cycle. The HGD system then identifies the source locations based on the average similarity score. The colors and sizes assigned to the source location indicators are based on the average similarity scores for the source locations.

Figure 3:
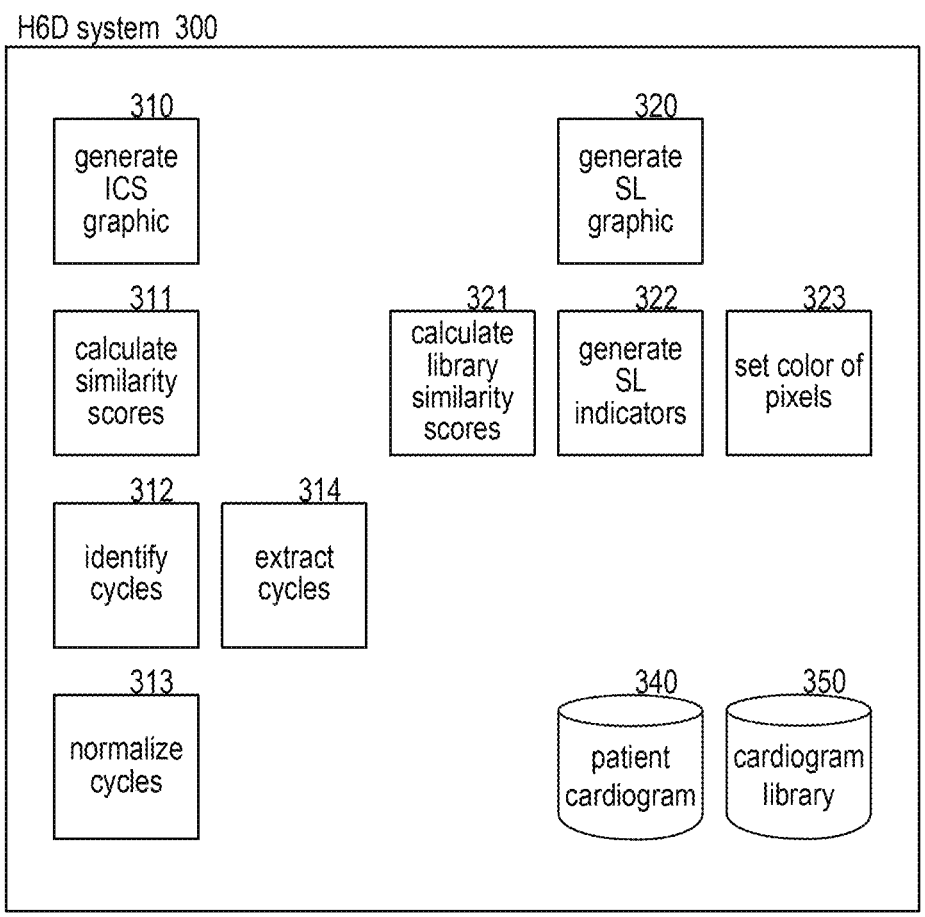
FIG. 3 is a block diagram illustrating components of the HTG system in some embodiments.

FIG. 3 is a block diagram illustrating components of the HGD system in some embodiments. The HGD system 300 includes components to generate an ICS graphic that include a generate ICS graphic component 310, a calculate similarity scores component 311, an identify cycles component 312, a normalize cycles component 313, and an extract cycles component 314. The generate ICS graphic component generates an ICS graphic for a patient cardiogram by invoking the calculate similarity scores component to calculate the similarity scores for pairs of patient cycles of a patient cardiogram, generating the ICS graphic based on the similarity scores, and outputting the ICS graphic. The calculate similarity scores component invokes the identify patient cycles component to identify patient cycles within the patient cardiogram, invokes the extract segments component to extract relevant segments from the patient cycles and discard not useful patient cycles, and then calculates the similarity score for each pair of patient cycles. The identify cycles component identifies patient cycles and invokes the normalize cycles component to normalize the patient cycles.

The HGD system also includes components to generate an SL graphic that include a generate SL graphic component 320, a calculate library similarity scores component 321, a generate source location indicators component 322, and a set color of pixels component 323. The generate SL graphics component invokes the calculate library similarity scores to calculate the similarity scores for each pair of a patient cycle and a library cycle, invokes the generate source library indicators component to generate the source library indicators for each patient cycle, receives a selection of patient cycles, invokes the set color of pixels component to populate the SL graphics based on the SL indicators associated with the received patient cycles, and then outputs the SL graphics. The calculate library similarity scores component calculates the similarity scores for each pair of a patient cycle and a library cycle and, for each patient cycle, sorts the source locations based on the similarity scores associated with the library cycles associated with the source locations. The generate source location indicators component generates, for each patient cycle, a source location indicator for each source location or a subset of the source locations such as those associated with the highest similarity scores. The set color of pixels component calculates the pixel values for overlapping regions of source location indicators.

The patient cardiogram data store 340 contains the patient cardiogram such as an electrocardiogram ("ECG") or a vectorcardiogram ("VCG"). The cardiogram library 350 contains library cycles of library cardiograms. The library cardiograms may be simulated cardiogram generated based on a computational model of the heart and/or a collection of patient cardiograms. The library cycles may have been identified in a manner similar to that of identifying the patient cycles. Each library cycle is associated to a corresponding source location or type. A cardiogram library may be generated using the techniques described in U.S. patent application Ser. No. 16/206,005, filed on Nov. 30, 2018 and entitled "Calibration of Simulated Cardiograms," which is hereby incorporated by reference.

The computing systems (e.g., network nodes or collections of network nodes) on which the HGD system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the simulations and training may be performed using a high-performance computing system, and the classifications may be performed by a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the HGD system and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The HGD system and the other described systems may be described in the general context of computer-executable instructions, such as program modules and components, executed by one or more computers, processors, or other devices. Generally, program modules or components include routines, programs, objects, data structures, and so on that perform tasks or implement data types of the HGD system and the other described systems. Typically, the functionality of the program modules may be combined or distributed as desired in various examples. Aspects of the HGD system and the other described systems may be implemented in hardware using, for example, an application-specific integrated circuit ("ASIC") or field programmable gate array ("FPGA").

The component of the HGD system may be implemented using a client-server model. For example, a client system may support receiving from a user a request for information on a heart, send to a server the request, and receive from the server indications of similarity scores. The client may then display a graphic that can be generated by the client based on the received indications of similarity scores or generated by and received from the server. The server may be hosted in a data center (e.g., cloud-based data center).

Figure 4:
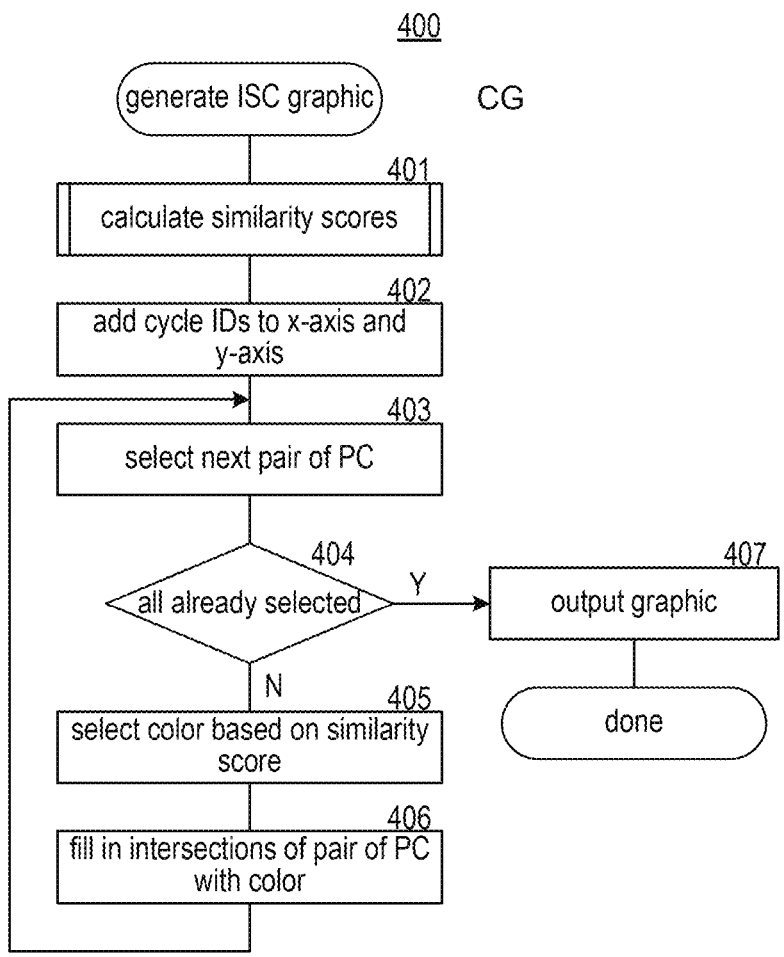
FIG. 4 is a flow diagram that illustrates the processing of a generate ICS similarity map in some embodiments.

FIG. 4 is a flow diagram that illustrates the processing of a generate ICS similarity map in some embodiments. A generate ICS similarity map component generates a similarity map for an ICS graphic based on similarity between either atrial segments or ventricular segments of patient cycles of a patient cardiogram ("CG"). In block 401, the component invokes a calculate similarity scores component to calculate the similarity scores between the patient cycles. In block 402, the component adds a label or identifier of the patient cycles to the x-axis and the y-axis. In similarity map 110 of FIG. 1, the labels "Beat 1," "Beat 3," and so on identify every other patient cycle rather than every cycle because of space limitations. In block 403, the component selects the next pair of patient cycles ("PC"). In decision block 404, if all the patient cycles have already been selected, then the component continues at block 407, else the component continues at block 405. In block 405, the component selects a color based on the similarity score for the pair of patient cycles. In block 406, the component fills in the intersections of the pair of patient cycles. For example, for the pair of patient cycle 22 and patient cycle 35, the component sets the intersections of (35, 22) and (22, 35) to blue indicating a relatively high similarity score for those patient cycles. The component then loops to block 403 to select the next pair of patient cycles. In block 407, the component may add a legend for the color range to the ICS graphic before outputting the ICS graphic. The component then completes.

The similarity map may also be displayed as a three-dimensional graph with the similarity score representing in the z-axis. In such a case, the HGD system allows the three-dimensional graph to be rotated to view the graph at different angles around the x-, y-, and z-axes.

Figure 5:
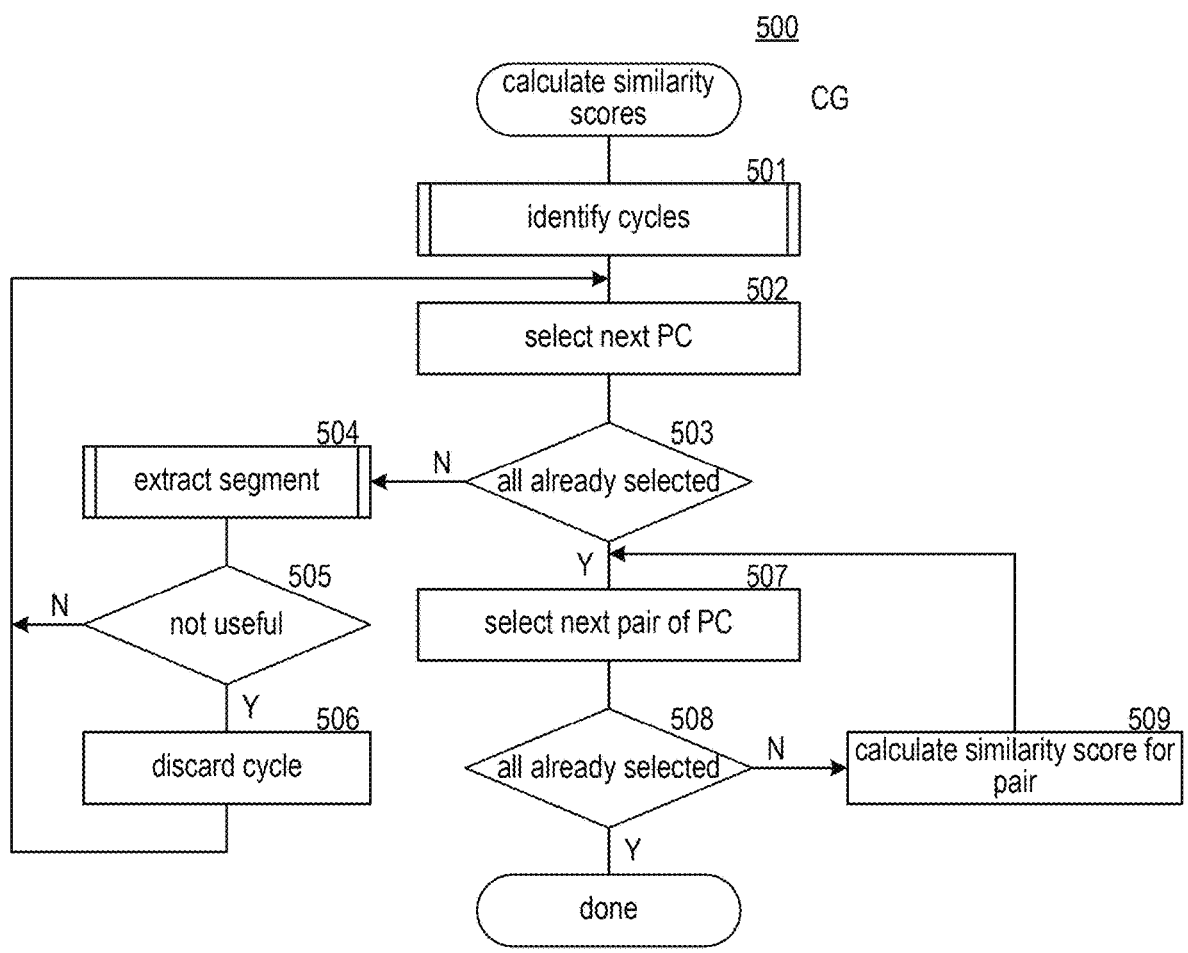
FIG. 5 is a flow diagram that illustrates processing of a calculate similarity scores component of the HGD system in some embodiments.

FIG. 5 is a flow diagram that illustrates processing of a calculate similarity scores component of the HGD system in some embodiments. The calculate similarity scored component 500 is invoked to calculate the similarity scores between patient cycles of a patient cardiogram. In block 501, the component invokes an identify cycles component to identify the patient cycles in a patient cardiogram. In blocks 502-506, the component loops identifying segments of the patient cycles and discarding those cycles that do not satisfy a usefulness criterion. A patient cycle may be not useful based on various criteria such being too short and/or too long. For example, a criterion may be that the patient cycle is longer than 500 ms and shorter than 1000 ms. In block 502, the component selects the next patient cycle. In decision block 503, if all the patient cycles have already been selected, then the component continues at block 507, else the component continues at block 504. In block 504, the component invokes an extract segment component to extract the relevant segments of the patient cycle. In decision block 505, if the patient cycle is indicated as not being useful by the extract segment component, then the component continues at block 506, else the component loops to block 502 to select the next patient cycle. In block 506, the component discards the patient cycle and loops to block 502 to select the next patient cycle. In blocks 507-509, the component loops calculating the similarity score between pairs of patient cycles. In block 507, the component selects the next pair of patient cycles. In decision block 508, if all the patient cycles have already been selected, then the component completes, else the component continues at block 509. In block 509, the component calculates the similarity score for the pair of patient cycles and then loops to block 507 to select the next pair of patient cycles.

In some embodiments, the HGD system may identify cycles (periodic intervals of arrhythmic activity) within an ECG or VCG. A cycle may be delimited by successive crossings from a negative voltage to a positive voltage ("positive crossings") or successive crossings from a positive voltage to a negative voltage ("negative crossings") with respect to a spatial direction or set of directions comprising a reference frame or set of reference frames. A reference frame may coincide with anatomical axes (e.g. left-to-right with x, superior-to-inferior with y, anterior-to-posterior with z), imaging axes (e.g. CT, MR, or x-ray coordinate frames), body-surface lead vectors, principal axes computed by principal component analysis of measured or simulated EM source configurations and outputs, or user-defined directions of interest. For example, a three-second VCG may have three cycles, and each cycle may be delimited by the times of the positive crossings along the x-axis. Alternatively, the cycles may be delimited by crossings along the y-axis or z-axis. In addition, cycles may be defined by negative crossings. The cycles may also be identified by processing by identifying an R peak and setting the end of the cycle to an estimate of the end of the T segment.

Figure 6:
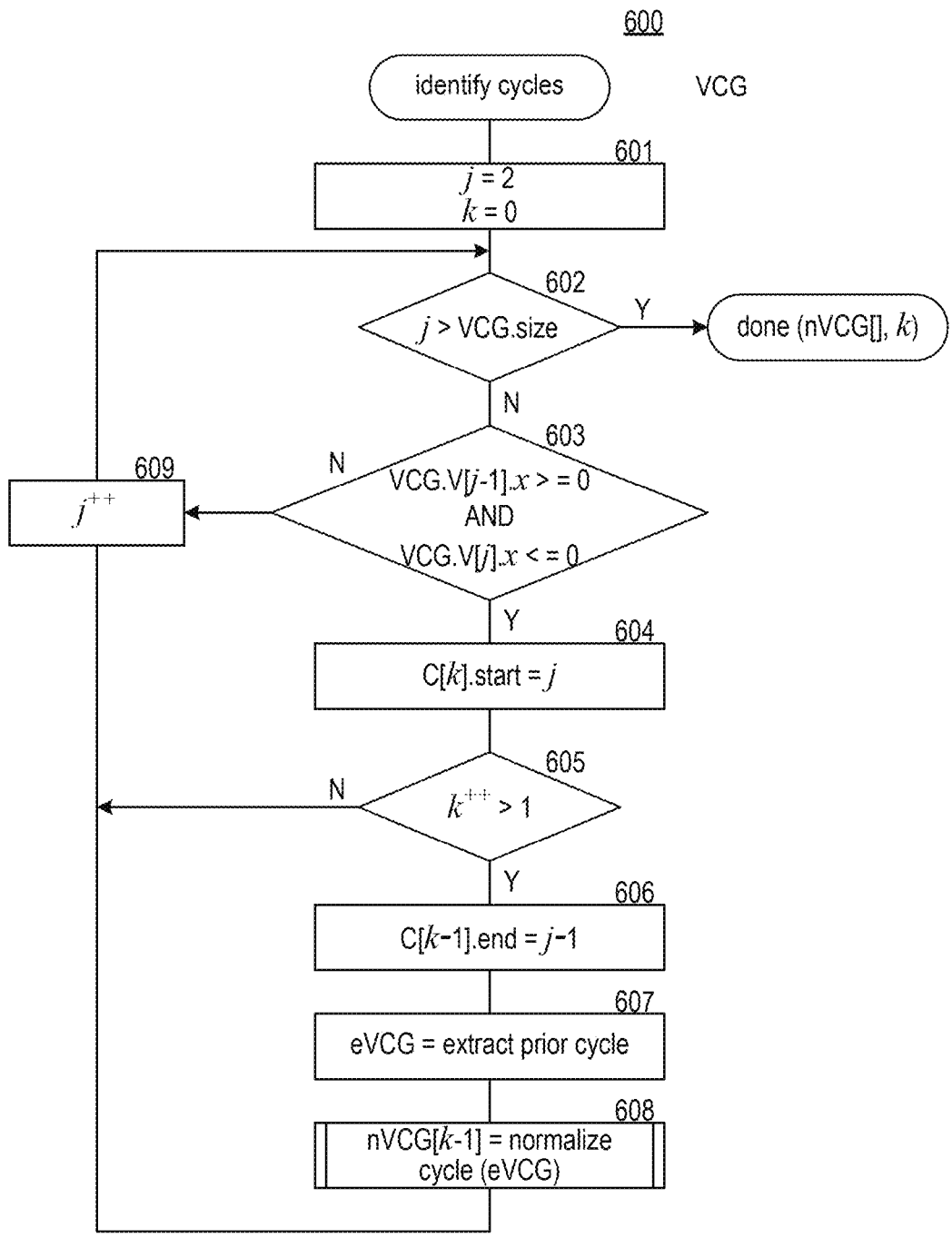
FIG. 6 is a flow diagram that illustrates the processing of an identify cycles component of the HGD system in some embodiments.

FIG. 6 is a flow diagram that illustrates the processing of an identify cycles component of the HGD system in some embodiments. The identify cycles component 600 is invoked to identify the cycles within a VCG and provides the normalized VCGs (nVCG[ ]) for the cycles. The component of FIG. 6 identifies cycles based on negative crossings of the x-axis. In block 601, the component initializes an index j to 2 for indexing through the VCG and sets an index k to 0 for indexing through the identified cycles. In decision block 602, if index j is greater than the size of the VCG, then the component has identified all the cycles and the component completes, providing the normalized nVCG, else the component continues at block 603. In block 603, if the prior voltage of the x-axis of the VCG (VCG.V[j−1].x) is greater than or equal to zero and the indexed voltage of the x-axis of the VCG (VCG.V[j].x) is less than zero (i.e., a negative crossing of the x-axis), then the start of a possible cycle has been identified and the component continues at block 604 to identify the cycle, else the component continues at block 609. In block 604, the component sets the start of the indexed cycle (C[k].start) equal to index j. In decision block 605, if at least one cycle has already been identified, then the end of the prior cycle is known and the component increments index k and continues at block 606, else the component increments index k and continues at block 609. In block 606, the component sets the end of the prior cycle to index j−1. In block 607, the component extracts the VCG (eVCG) for the prior indexed cycle delimited by the start and the end of the prior cycle. In block 608, the component invokes a normalize cycle component, passing an indication of the extracted VCG (eVCG), and receives the normalized cycle (nVCG). In block 609, the component increments the index j for indexing through the VCG and loops to block 602.

Figure 7:
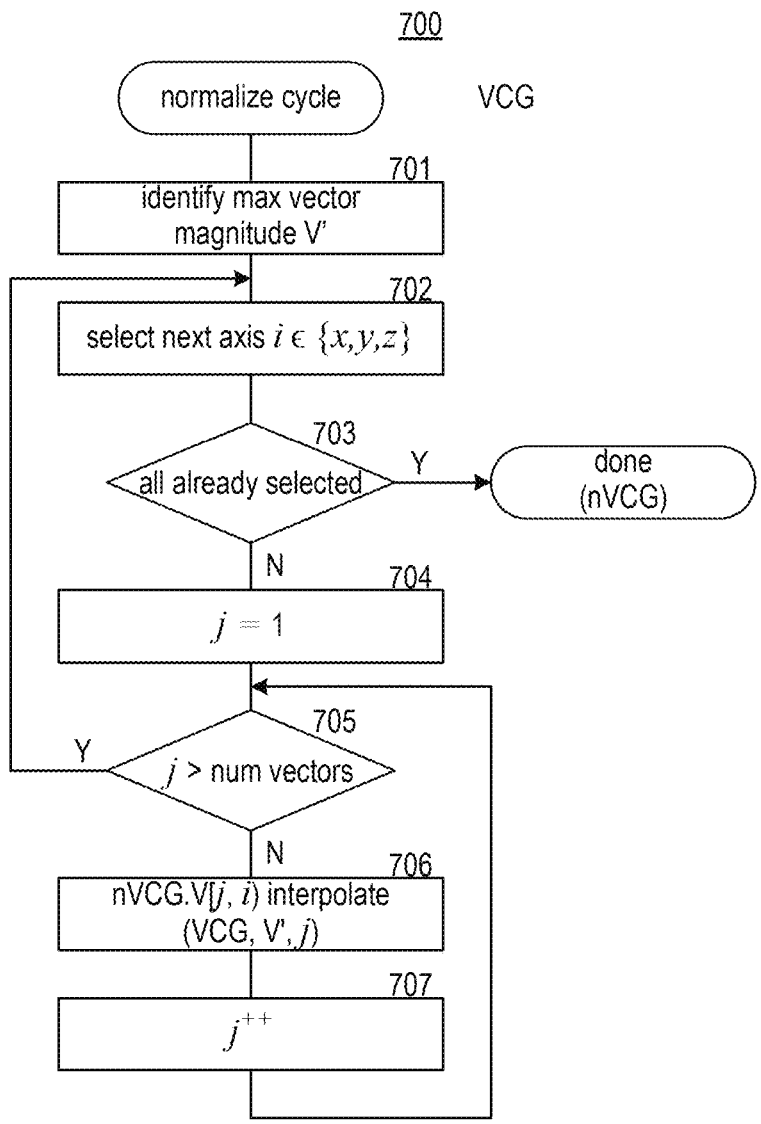
FIG. 7 is a block diagram that illustrates the processing of a normalize cycle component of the HGD system in some embodiments.

FIG. 7 is a block diagram that illustrates the processing of a normalize cycle component of the HGD system in some embodiments. The normalize cycle component 700 is invoked, passing an indication of the VCG of a cycle, and normalizes the cycle. If the cycles are of an ECG, then the cycles can be normalized in time and voltage to value between 0 and 1. In block 701, the component identifies the maximum vector magnitude V' of the vectors in the cycle. For example, a vector magnitude of a vector may be calculated by taking the square root of the sum of the squares of the x, y, and z values of the vector. In block 702, the component sets index i to index a next axis of the VCG. In decision block 703, if all the axes have already been selected, then the component completes, providing the normalized VCG, else the component continues at block 704. In block 704, the component initializes an index j to 1 for indexing through the vectors of a normalized cycle. In decision block 705, if index j is greater than the number of vectors of a normalized cycle, then the component loops to block 702 to select the next axis, else the component continues at block 706. In block 706, the component sets the normalized VCG for the indexed vector for the indexed axis to an interpolation of the passed VCG, the indexed vector, and the maximum vector magnitude V'. The interpolation effectively compresses or expands the VCG to the number of vectors in the normalized VCG and divides the x, y, and z values of the vector by the maximum vector magnitude V'. In block 707, the component increments the index j and then loops to block 705.

Figure 8:
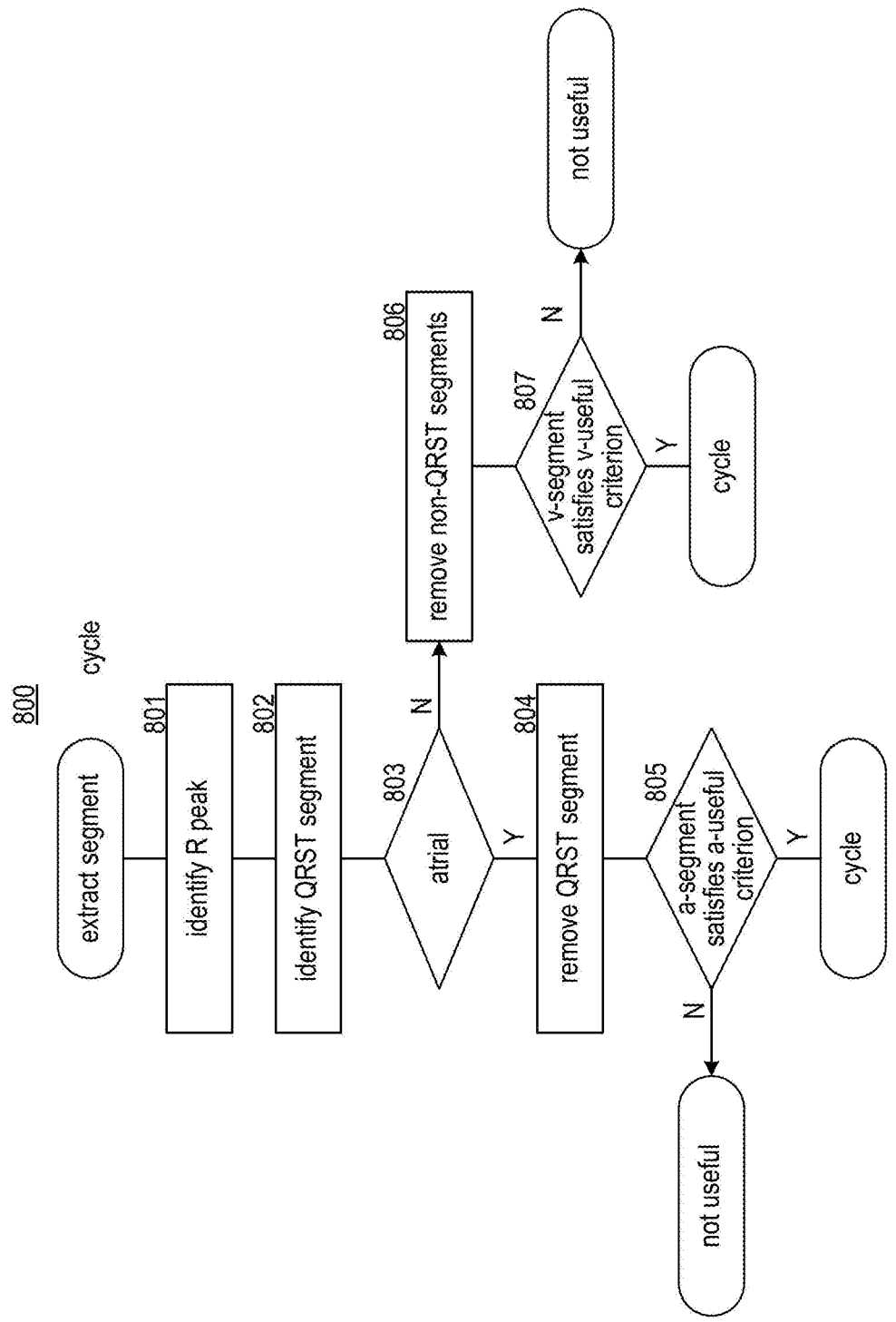
FIG. 8 is a flow diagram that illustrates the processing of an extract segment component of the HGD system in some embodiments.

FIG. 8 is a flow diagram that illustrates the processing of an extract segment component of the HGD system in some embodiments. The extract segment component 800 extracts the relevant portion of a cycle depending on whether an atrial or ventricular analysis is being performed. In block 801, the component identifies the R peak of the cycle. For example, the component may apply a Pan-Tompkins-type algorithm. (See, Pan, J., Tompkins, W. J. "A Real-Time QRS Detection Algorithm". IEEE Transactions on Biomedical Engineering (3): 230 (1985).) In block 802, the component identifies the QRST segment. Once the R peak is identified, various techniques may be used to identify the QRST segment (i.e., QT interval). One technique is to use a fixed window that is a certain time before the R peak and a certain time after the R peak such as 30 ms before and 250 ms after. Another technique may also be based on manual identification of the QRST segment in which case the R peak may not be separately identified. Another technique may algorithmically identify the QRST segment factoring the heart rate.

Another technique may algorithmically identify the R onset or T offset factoring rates of voltage change. In decision block 803, if the atrial segment is to be identified, then the component continues at block 804, else the component continues at block 806. In block 804, the component removes the QRST segment from the cycle resulting in the atrial segments remaining. In decision block 805, if the atrial segments satisfy an atrial useful criterion, then the component continues indicating the cycle with the QRST segment removed, else the component completes indicating that the atrial segments are not useful. An atrial useful criterion may be that the atrial segments of the cycle have length that are within a minimum and maximum time such as 500 and 1000 ms. In block 806, the component removes the non-QRST segments from the cycle. In decision block 807, if the QRST segment satisfies a ventricular useful criterion, then the component completes indicating the cycle with the non-QRST segments removed, else the component completes indicating that the QRST segment is not useful. The component may remove a segment of a cycle represented by an ECG by setting the values corresponding to the segment to zero.

Figure 9:
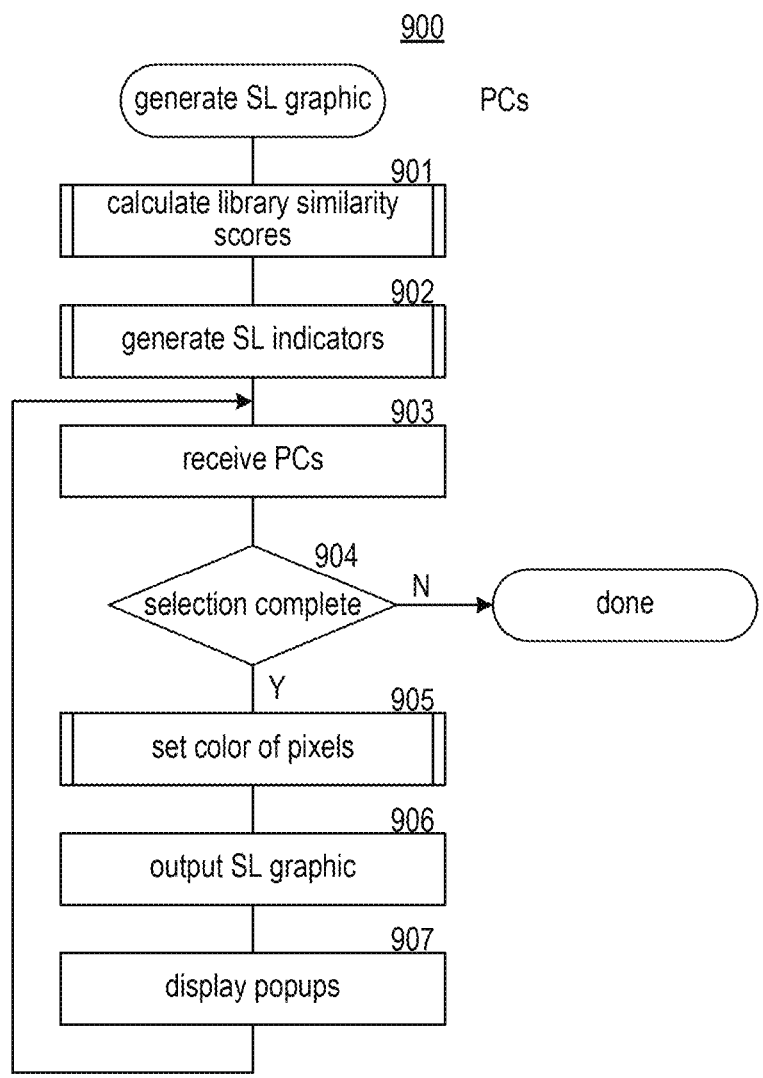
FIG. 9 is a flow diagram that illustrates the processing of a generate source location graphic of the HGD system in some embodiments.

FIG. 9 is a flow diagram that illustrates the processing of a generate source location graphic of the HGD system in some embodiments. A generate SL graphic component 900 inputs a patient cycle and outputs SL graphics for selected sets of patient cycles. In block 901, the component invokes a calculate library similarity scores component to generate the similarity scores for pairs of patient cycles and library cycles. In block 902, the component invokes a generate source location indicators to generate the indicators of source locations for each patient cycle. In block 903, the component receives a selection of a set of one or more patient cycles. A user may make the selection using cycle selection box 230 of SL graphic 200. The selection may also be received from a software system that interfaces with the HGD system, a data store, and so on. In decision block 904, if no more sets of patient cycles are to be selected, then the component completes, else the component continues at block 905. In block 905, the component invokes a set color of pixels component to set the color for each pixel of the SL graphic for the selected patient cycles. In block 906, the component outputs the SL graphic. In block 907, the component displays popups as a cursor moves to different locations on the SL graphic. For example, when the cursor is moved over a source location indicator, a popup may be displayed that include statistics relating to patient cycles associated with the corresponding source location such as the average similarity score of the highest similarity scores of those cycles. The component then loops to block 903 to receive a selection of patient cycles. In some embodiments, the SL graphic may be three-dimensional, and the HGD system may support three-dimensional rotation of the SL graphic so that a person can view, for example, the inside, front, and back of the heart.

Figure 10:
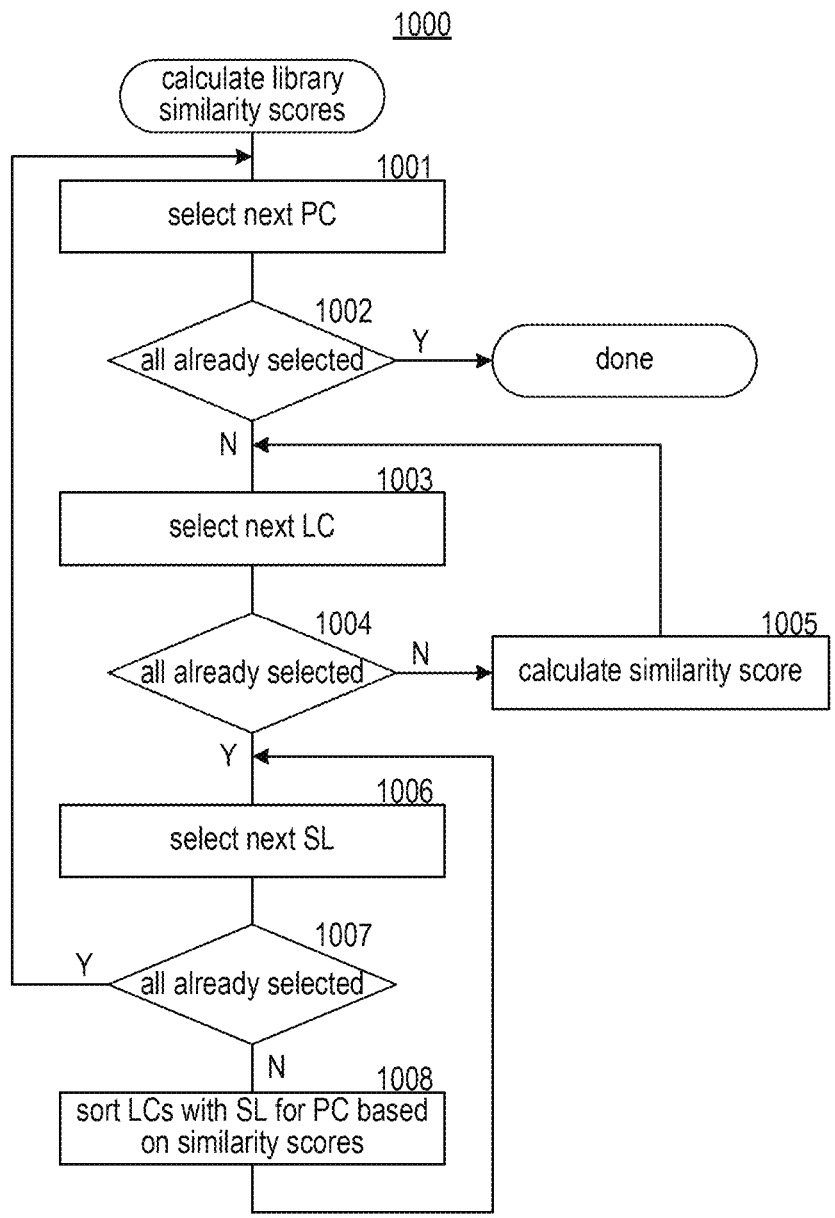
FIG. 10 is a flow diagram that illustrates processing of a calculate library similarity scores component of the HGD in some embodiments.

FIG. 10 is a flow diagram that illustrates the processing of a calculate library similarity scores component of the HGD system in some embodiments. The calculate library similarity score component 1000 calculates the similarity scores pairs of patient cycles and library cycles and, for each patient cycle, sorts the similarity scores of the patient cycles associated with each source location. In block 1001, the component selects the next patient cycle. In decision block 1002, if all the patient cycles have already been selected, then the component completes, else the component continues at block 1003. In block 1003, the component selects the next library cycle ("LC"). In decision block 1004, if all the library cycles have already been selected for the selected patient cycle, then the component continues at block 1006, else the component continues at block 1005. In block 1005, the component calculates the similarity score for the patient cycle and the library cycle and continues at block 1003. In blocks 1006-1008, the component loops sorting the library cycles for each source location. In block 1006, the component selects the next source location. In decision block 1007, if all the source locations have already been selected for the patient cycle, then the component loops to block at block 1001 to select the next patient cycle, else the component continues at block 1008. In block 1008, the component sorts the library cycles associated with the selected source location for the selected patient cycle based on the similarity scores for those library cycles and the selected patient cycle. The component then loops to block 1006 to select the next source location.

Figure 11:
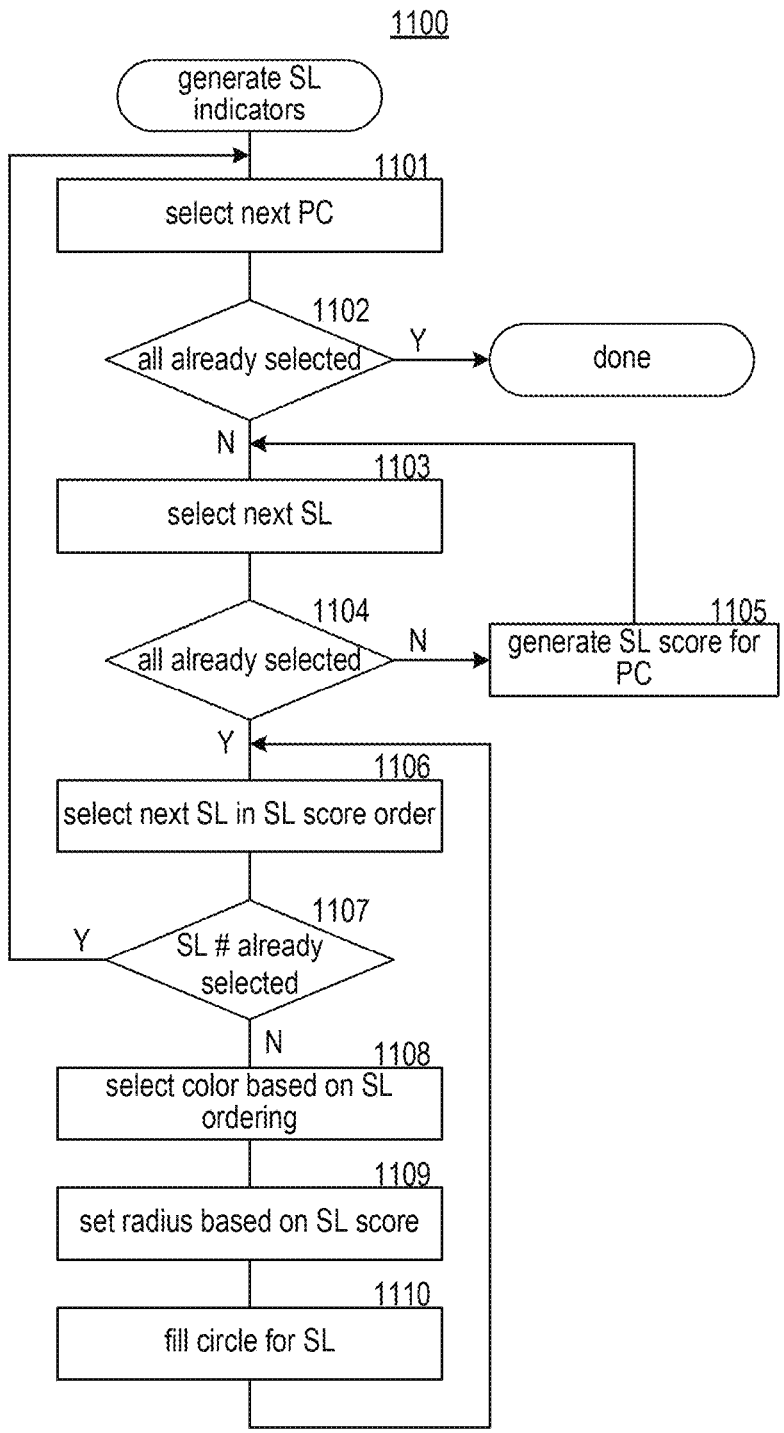
FIG. 11 is a flow diagram that illustrates the processing of a generate source location indicators component of the HGD the system in some embodiments.

FIG. 11 is a flow diagram that illustrates the processing of a generate source location indicators component of the HGD the system in some embodiments. A generate source location indicators component generates the source location indicators for each patient cycle. In block 1101, the component selects the next patient cycle. In decision block 1102, if all the patient cycles have already been selected, then the component completes, else the component continues at block 1103. In block 1103, the component selects the next source location. In decision block 1104, if all the source locations have already been selected, then the component continues at block 1106, else the component continues at block 1105. In block 1105, the component generates a source location score for the selected patient cycle. For example, the source location score may be the highest similarity score for a library cycle (and the selected patient cycle) associated with that source location. As another example, the source location score may be the average of the five highest similarity scores. In block 1106, the component selects the next source location in source location score order. In decision block 1107, if the number of source locations whose source location indicators that are to be included in the SL graphic has already been selected, then the component continues at block 1101, else the component continues at block 1108. In block 1108, the component sets the color for the source location based on the source location ordering. In block 1109, the component sets the radius for the source location based on the source location score. In block 1110, the component fills a data structure representing the circle for the source location based on the color and the radius. The component then loops to block 1106 to select the next source location.

Figure 12:
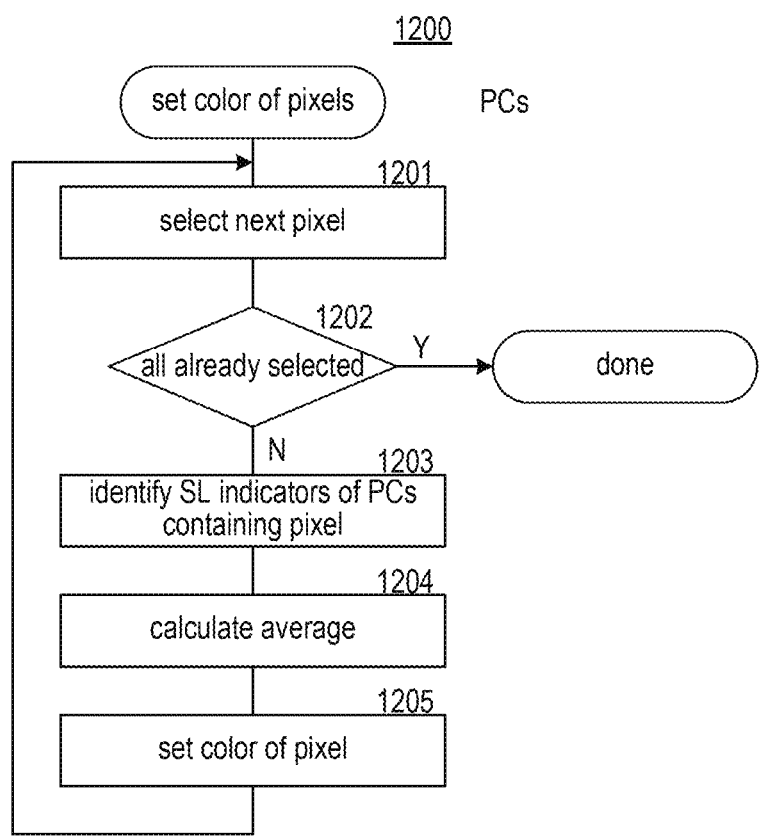
FIG. 12 is a flow diagram that illustrates the processing of a set color of pixels component of the HGD system in some embodiments.

FIG. 12 is a flow diagram that illustrates the processing of a set color of pixels component of the HGD system in some embodiments. A set color of pixels component 1200 is provided patient cycles and calculates the color of each pixel for the SL graphics based on the source location indicators for the patient cycles. In block 1201, the component selects the next pixel of the SL graphic. In decision block 1202, if all the pixels of already been selected, then the component completes, else the component continues at block 1203. In block 1203, the component identifies the source location indicators of the patient cycles that contain the selected pixel. In block 1204, the component calculates an average of the identified source location indicators based on the data structures representing the circles for the source locations. In block 1205, the component sets the color of the pixel based on the average and then loops to block 1201 to select the next pixel.

The following paragraphs describe various embodiments of aspects of the HGD system. An implementation of the HGD system may employ any combination of the embodiments. The processing described below may be performed by a computing system with a processor that executes computer-executable instructions stored on a computer-readable storage medium that implements the HGD system.

Intra-Cardiogram Similarity

In some embodiments, a method performed by one or more computing systems is provided for presenting information to assist evaluation of an electromagnetic ("EM") source of a body. The method accesses indications of cycles within EM measurements of an EM field of the EM source, each pair of cycles having a similarity score indicating similarity between the cycles of the pair. The method generates a graphic indicating the similarity score for each pair of cycles. The method outputs the graphic to an output device. In some embodiments, the cycles have an ordering, the graphic includes a map with first axis representing each cycle as ordered and a second axis representing each cycle as ordered, and an intersection of a pair of cycles provides an indication of the similarity score for the pair of cycles. In some embodiments, the indications of similarity scores are based on varying a graphic characteristic. In some embodiments, the graphic characteristic is based on color. In some embodiments, the graphic characteristic is based on intensity level. In some embodiments, the graphic further includes a third axis representing similarity score and wherein the indication of the similarity score for a pair of cycles is based on height along the third axis. In some embodiments, the method rotates the graphic. In some embodiments, the output device is a display device, and the method receives a selection of a pair of cycles and displaying information relating the selected pair of cycles. In some embodiments, the display information includes the similarity score for the selected pair of cycles. In some embodiments, the output device is a display device and further comprising receiving a selection of multiple pairs of cycles and displaying information relating the selected multiple pair of cycles. In some embodiments, the displayed information includes average similarity score, standard deviation of the similarity scores, a stability index, or a number of groups of pairs of similar cycles. In some embodiments, the EM source is a heart and the EM measurements are represented by a cardiogram. In some embodiments, the indications of similarity scores are based on varying a graphic characteristic. In some embodiments, the EM measurements are generated based on a computational model that models EM activations of the EM source.

In some embodiments, one or more computing systems are provided for presenting information to assist evaluation of a heart of a patient. The one or more computing systems comprises one or more computer-readable storage mediums for storing computer-executable instructions and one or more processors for executing the computer-executable instructions stored in the one or more computer-readable storage mediums. When executed, the instructions to access indications of cycles within a cardiogram of the patient. Each pair of cycles has a similarity score indicating similarity between the cycles of the pair. The instructions generate a graphic indicating the similarity score for each pair of cycles. The instructions display the graphic via a display device. In some embodiments, the cycles have an ordering within the cardiogram, the graphic includes a map with first axis representing each cycle as ordered and a second axis representing each cycle as ordered, and an intersection of a pair of cycles provides an indication of the similarity score for the pair of cycles. In some embodiments, the indications of similarity scores are based on varying a graphic characteristic. In some embodiments, the graphic characteristic is based on color. In some embodiments, graphic characteristic is based on intensity level. In some embodiments, the graphic further includes a third axis representing similarity score and wherein the indication of the similarity score for a pair of cycles is based on height along the third axis. In some embodiments, the instructions further receive a selection of a pair of cycles and display information relating the selected pair of cycles. In some embodiments, the display information includes the similarity score for the selected pair of cycles. In some embodiments, the instructions further receive a selection of multiple pairs of cycles and displaying information relating the selected multiple pair of cycles. In some embodiments, the displayed information includes average similarity score, standard deviation of the similarity scores, a stability index, or a number of groups of pairs of similar cycles. In some embodiments, the instructions further identify the cycles of the cardiogram. In some embodiments, the instructions further calculate the similarity score for each pair of cycles.

In some embodiments, one or more computing systems is provided for presenting information relating to a heart. The one or more computing systems comprise one or more computer-readable storage mediums storing computer-executable instructions and one or more processors for executing the computer-executable instructions stored in the one or more computer-readable storage mediums. When executed, the instructions receive from a user a request for the information relating to the heart. The instructions send to a server a request for the information. The instructions receive from the server the information indicating a similarity score for each pair of cycles of electrical activations of the heart. The similarity score for a pair of cycles indicating similarity between the cycles of the pair. The instructions display on a display device visual indications of the similarity scores of the received information. In some embodiment, the cycles have an ordering, the graphic includes a map with a first axis representing each cycle as ordered and a second axis representing each cycle as ordered, and an intersection of a pair of cycles provides the visual indication of the similarity score for the pair of cycles. In some embodiments, the instructions further generate the graphic. In some embodiments, the request is sent to and the received information is received from a server. In some embodiments, the request is sent to and the received information is received from a cloud-based system. In some embodiments, the received information includes the graphic. In some embodiments, a visual indication is non-textual.

Source Location

In some embodiments, a method performed by one or more computing systems is provided for presenting information to assist evaluation of an electromagnetic ("EM") source of a patient. The method accesses a library having library cycles of library EM measurements of an EM field of the EM source. Each library cycle is associated with a source location of the EM source. The method, for each of a plurality of library cycles, calculates a similarity score for the library cycle indicating similarity between the library cycle and a patient cycle of patient EM measurements of the patient. The method identifies a source location associated with a target library cycle based on the similarity score of the target library cycle. The method generates a graphic that includes a representation of a portion of the EM source and a source location indicator located based on the identified source location. The source location indicator has a characteristic that is based on the similarity score associated with the target library cycle. The method outputs the graphic to an output device. In some embodiments, the characteristic is size of the source location indicator that is based on the similarity score. In some embodiments, the source location indicator is a circle and the size indicates the radius of the circle. In some embodiments, a smaller size indicates a higher similarity score. In some embodiments, the characteristic is color. In some embodiments, the source location indicator is a circle, and a characteristic is size of the circle and a characteristic is color. In some embodiments, the color varies from the center of the circle to the circumference of the circle. In some embodiments, the patient cycle is one of a plurality of patient cycles and for each patient cycle generating a graphic and outputting the graphics in sequence to animate the locations of the source locations. In some embodiments, multiple source locations are associated with target library cycles are identified based on the similarity scores of the target library cycles and the graphic includes source location indicators located based on the identified source locations, each source location indicator with a characteristic that is based on the similarity score associated with a target library cycle. In some embodiments, the characteristic is size of the source location indicators, and the sizes are based on the similarity scores of the identified library cycles. In some embodiments, a smaller size indicates a higher similarity score. In some embodiments, characteristic is color with each source location indicator having a different color. In some embodiments, when source location indicators overlap on the graphic, the color of the overlap is based on a combination of the color of the source location indicators that overlap. In some embodiments, the source location indicators are circles and a characteristic is size of the circles and a characteristic is color that indicates an ordering of a source location score that is based on the similarity scores of the target library cycles. In some embodiments, the color of a circle is at the center and the coloring of the circle varies from the center to the circumference. In some embodiments, the method receives a selection of the patient cycles specified by a person. In some embodiments, the method identifies the patient cycles. In some embodiments, the method outputs statistics relating to the identified target cycle. In some embodiments, the identifying identifies source locations associated with target library cycles based on the similarity scores of the target library cycles and the graphic includes source location indicators for the identified source locations. In some embodiments, the EM measurements are generated based on a computational model that models EM activation of the EM source. In some embodiments, the EM source is a heart and the EM measurements are represented by a cardiogram. In some embodiments, the source location relates to an abnormal electrical activation of the heart and further comprising displaying a source type indicator indicate the source type of the abnormal electrical activation. In some embodiments, the source type is selected from a group consisting of rotor, focal, fibrillation, tachycardia, and flutter.

In some embodiments, one or more computing systems are provided for presenting information to assist evaluation of a heart of a patient. The one or more computing systems comprise one or more computer-readable storage mediums for storing computer-executable instructions and one or more processors for executing the computer-executable instructions stored in the one or more computer-readable storage mediums. When executed, the instructions, for each of a plurality of library cycles of a library, calculate a similarity score for the library cycle indicating similarity between the library cycle and a patient cycle of patient cardiogram of the patient. Each library cycle is associated with a source location of the heart. The instructions identify a source location associated with a target library cycle based on the similarity score of the target library cycle. The instructions generate a graphic that includes a representation of a portion of a heart and a source location indicator located on the heart based on the identified source location. The source location indicator has a characteristic that is based on the similarity score associated with the target library cycle. The instructions display the graphic via a display device. In some embodiments, the characteristic is size of the source location indicator that is based on the similarity score. In some embodiments, the source location indicator is a circle, and the size indicates the radius of the circle. In some embodiments, a smaller size indicates a higher similarity score. In some embodiments, the characteristic is color. In some embodiments, the source location indicator is a circle, characteristic is size of the circle, and a characteristic is color. In some embodiments, the color varies from the center of the circle to the circumference of the circle. In some embodiments, the patient cycle is one of a plurality of patient cycles, and the instructions generates a graphic for each patient cycle and display the graphics in sequence to animate changes in the source locations of the patient cycles. In some embodiments, the instructions identify source locations associated with target library cycles based on the similarity scores of the target library cycles and to generate the graphic to include source location indicators located based on the identified source locations, each source location indicator having a characteristic that is based on the similarity score associated with a target library cycle. In some embodiments, the characteristic is size of the source location indicators, and the sizes being based on the similarity scores of the identified library cycles. In some embodiments, a smaller size indicates a higher similarity score. In some embodiments, the characteristic is color with each source location indicator having a different color. In some embodiments, when source location indicators overlap on the graphic, the color of the overlap is based on a combination of the color of the source location indicators that overlap. In some embodiments, the source location indicators are circles, a characteristic is size of the circles, a characteristic is color that indicates an ordering of a source location score that is based on the similarity scores of the target library cycles. In some embodiments, the color of a circle is at the center and the coloring of the circle varies from the center to the circumference. In some embodiments, the instructions display statistics relating to the identified target cycle. In some embodiments, the identifying identifies source locations associated with target library cycles based on the similarity scores of the target library cycles, and the graphic includes source location indicators for the identified source locations. In some embodiments, at least some of the library cycles are generated based on a computational model that models electrical activation of the heart. In some embodiments, at least some of the library cycles of cardiograms collected from people. In some embodiments, the source location relates to an abnormal electrical activation of the heart and the instructions display a source type indicator indicate the source type of the abnormal electrical activation. In some embodiments, the source type is selected from a group consisting of rotor, focal, fibrillation, tachycardia, and flutter.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

I claim:

1. A method performed by one or more computing systems for presenting information to assist evaluation of an electromagnetic ("EM") source of a body, the method comprising:
   accessing indications of cycles within EM measurements of an EM field of the EM source, each pair of cycles having a similarity score indicating similarity between the cycles of the pair;
   generating a graphic indicating the similarity score for each pair of cycles; and
   outputting the graphic to an output device
   wherein the cycles have an ordering, wherein the graphic includes a map with first axis representing each cycle as ordered and a second axis representing each cycle as ordered, and wherein an intersection of a pair of cycles on the map provides visual indication of the similarity score for the pair of cycles.

2. The method of claim 1 wherein the visual indications of similarity scores are based on varying a graphic characteristic.

3. The method of claim 2 wherein the graphic characteristic is based on color.

4. The method of claim 2 wherein the graphic characteristic is based on intensity level.

5. The method of claim 1 wherein the graphic further includes a third axis representing similarity score and wherein the visual indication of the similarity score for a pair of cycles is based on height along the third axis.

6. The method of claim 5 further comprising rotating the graphic.

7. The method of claim 1 wherein the output device is a display device and further comprising receiving a selection of a pair of cycles and displaying information relating the selected pair of cycles.

8. The method of claim 7 wherein the displayed information includes the similarity score for the selected pair of cycles.

9. The method of claim 1 wherein the output device is a display device and further comprising receiving a selection of multiple pairs of cycles and displaying information relating the selected multiple pair of cycles.

10. The method of claim 9 wherein the displayed information includes average similarity score, standard deviation of the similarity scores, a stability index, or a number of groups of pairs of similar cycles.

11. The method of claim 1 wherein the EM source is a heart and the EM measurements are represented by a cardiogram.

12. The method of claim 1 wherein the EM measurements are generated based on a computational model that models EM activations of the EM source.

13. One or more computing systems for presenting information relating to a heart of a patient, the one or more computing systems comprising:
   one or more computer-readable storage mediums storing computer-executable instructions for controlling the one or more computing systems to:
      access indications of cycles within a cardiogram of the patient, each pair of cycles having a similarity score indicating similarity between the cycles of the pair;
      generate a graphic indicating the similarity score for each pair of cycles; and
      display the graphic via a display device;
      wherein the cycles have an ordering within the cardiogram, wherein the graphic includes a map with a first axis representing each cycle as ordered and a second axis representing each cycle as ordered, and wherein an intersection of a pair of cycles on the map provides a visual indication of the similarity score for the pair of cycles; and
   one or more processors for executing the computer-executable instructions stored in the one or more computer-readable storage mediums.

14. The one or more computing systems of claim 13 wherein the visual indications of similarity scores are based on varying a graphic characteristic.

15. The one or more computing systems of claim 14 wherein the graphic characteristic is based on color.

16. The one or more computing systems of claim 14 wherein the graphic characteristic is based on intensity level.

17. The one or more computing systems of claim 13 wherein the graphic further includes a third axis representing similarity score and wherein the indication of the similarity score for a pair of cycles is based on height along the third axis.

18. The one or more computing systems of claim 13 wherein the instructions further control the one or more computing systems to receive a selection of a pair of cycles and display information relating the selected pair of cycles.

19. The one or more computing systems of claim 18 wherein the display information includes the similarity score for the selected pair of cycles.

20. The one or more computing systems of claim 13 wherein the instructions further control the one or more computing systems to receive a selection of multiple pairs of cycles and display information relating the selected multiple pair of cycles.

21. One or more computing systems for presenting information relating to a heart, the one or more computing systems comprising:
   one or more computer-readable storage mediums storing computer-executable instructions for controlling the one or more computing systems to:
      receive from a user a request for the information relating to the heart;
      send to a server a request for the information;
      receive from the server the information, the received information indicating a similarity score for each pair of cycles of electrical activations of the heart, the similarity score for a pair of cycles indicating similarity between the cycles of the pair; and
      display on a display device visual indications of the similarity scores of the received information;
      wherein the cycles have an ordering, wherein the visual indications are displayed as a graphic that includes a map with a first axis representing each cycle as ordered and a second axis representing each cycle as ordered, and wherein an intersection of a pair of cycles on the map provides the visual indication of the similarity score for the pair of cycles; and
   one or more processors for executing the computer-executable instructions stored in the one or more computer-readable storage mediums.

22. The one or more computing systems of claim 21 wherein the instructions further generate the graphic.

23. The one or more computing systems of claim 21 wherein the instructions further control the one or more computing systems to receive from the user a selection of a pair of cycles and display information relating the selected pair of cycles.

24. The one or more computing systems of claim 21 wherein the server is hosted by a cloud-based system.

25. The one or more computing systems of claim 21 wherein the received information includes the graphic.

26. The one or more computing systems of claim 21 wherein a visual indication is non-textual.

* * * * *